United States Patent
Izmailov

(10) Patent No.: US 6,582,577 B1
(45) Date of Patent: Jun. 24, 2003

(54) ELECTROPHORESIS GEL CASSETTE

(75) Inventor: Alex Izmailov, Etobicoke (CA)

(73) Assignee: Visible Genetics Inc., Toronto (CA)

( * ) Notice: Subject to any disclaimer, the term of this patent is extended or adjusted under 35 U.S.C. 154(b) by 259 days.

(21) Appl. No.: 09/652,331

(22) Filed: Aug. 31, 2000

(51) Int. Cl.⁷ .................... C02F 1/40; C02F 11/00; C25B 11/00; C25B 13/00; C25B 9/00; G01N 27/27; G01N 27/403; G01N 27/453

(52) U.S. Cl. ................ 204/618; 204/600; 204/616; 204/606; 204/620

(58) Field of Search ................ 204/618, 600, 204/616, 606, 620

(56) References Cited

U.S. PATENT DOCUMENTS

| | | |
|---|---|---|
| 4,169,036 A | 9/1979 | Anderson et al. |
| 4,574,040 A * | 3/1986 | Delony et al. ........... 204/606 |
| 4,820,398 A | 4/1989 | Yamamoto |
| 4,861,411 A | 8/1989 | Tezuka |
| 5,073,246 A | 12/1991 | Chu et al. |
| 5,149,417 A | 9/1992 | Foley et al. |
| 5,186,807 A | 2/1993 | Sanford et al. |
| 5,192,408 A | 3/1993 | Scott |
| 5,217,591 A | 6/1993 | Gombocz et al. |
| 5,228,970 A | 7/1993 | Foley |
| 5,281,322 A | 1/1994 | Antoinette et al. |
| 5,304,292 A * | 4/1994 | Jacobs et al. ........... 204/467 |
| 5,324,412 A | 6/1994 | Kolner |
| 5,374,527 A | 12/1994 | Grossman |
| 5,384,025 A | 1/1995 | Blasband |
| 5,464,515 A | 11/1995 | Bellon |
| 5,514,255 A | 5/1996 | Gautsch |
| 5,525,202 A | 6/1996 | Evans et al. |
| 5,543,023 A | 8/1996 | Lugojan |
| 5,618,399 A | 4/1997 | Gautsch et al. |
| 5,628,891 A | 5/1997 | Lee |
| 5,736,022 A | 4/1998 | Axelsson |
| 5,746,901 A | 5/1998 | Balch et al. |
| 5,800,691 A | 9/1998 | Kozulic |
| 5,843,295 A | 12/1998 | Steiner et al. |
| 5,858,189 A | 1/1999 | Williams |
| 5,885,431 A * | 3/1999 | Renfrew et al. ........... 204/465 |
| 5,972,188 A | 10/1999 | Rice et al. |
| 5,993,628 A | 11/1999 | Selby et al. |
| 6,017,436 A | 1/2000 | Kozulic |
| 6,024,854 A | 2/2000 | Gilchrist |
| 6,054,036 A * | 4/2000 | Izmailov et al. ........... 204/606 |
| 6,328,870 B1 * | 12/2001 | Provonchee et al. ........ 204/466 |
| 6,379,519 B1 * | 4/2002 | Sevigny et al. ............ 204/620 |

FOREIGN PATENT DOCUMENTS

WO    WO 9610743 A1 *    4/1996    ......... G01N/27/447

* cited by examiner

Primary Examiner—Jill Warden
Assistant Examiner—Jennine Brown
(74) Attorney, Agent, or Firm—Oppedahl & Larson LLP

(57) ABSTRACT

An electrophoresis cassette is made from two substrates separated by spacers, and a one-piece molded plastic edge adapter. The edge adapter provides the contoured edge to facilitate sample loading, and because it is made from molded plastic is easier to make. Furthermore, the edge adapter has vertically extending arms which define the sides of the loading region and which, when glued to the back substrate, prevent leakage of buffer solution from the region surrounding the electrophoresis origin. In one variation, a groove in the bottom edge of the edge adapter receives the top edge of the front substrate to further define the position of the edge adapter in relation to the substrate. Vertical divider fins may optionally be formed on the contoured surface of the edge adapter. These divider fins define loading wells for the introduction of sample into the lanes of the electrophoresis gel.

26 Claims, 4 Drawing Sheets

ELECTROPHORESIS GEL CASSETTE

BACKGROUND OF THE INVENTION

This application relates to an improved design for an electrophoresis gel cassette.

Gel electrophoresis is a powerful analytic tool, which is used routinely in the analysis of nucleic acid sequences. Such analyses are now shifting from the research environment to become a part of the battery of tests performed by diagnostic laboratories. With this shift has come a need for simplified and less expensive gel cassettes.

The basic gel cassette is formed from two parallel plates held apart by spacers to define a gel cavity. One edge of the front plate may be lower than the back plate, and this edge of the front plate may be beveled or otherwise contoured to facilitate loading. (see, for example, U.S. Pat. No. 5,993,628 and 5,627,022). Because the plates are generally made from glass (to minimize interference with fluorescent detection and/or gel polymerization that could occur if plastics were used, the formation of this beveled or contoured edge during manufacturing can be expensive and time-consuming. Furthermore, the edge is prone to breakage in shipment and subsequent handling. Defects in the edge, such as chips or ripples, or a rough surface at the beveled edge can be translated into defects in the gel. Thus, quality control on this edge is a significant element in the overall cost of the gel cassette.

SUMMARY OF THE INVENTION

In accordance with the present invention, an electrophoresis cassette is made from two substrates separated by spacers, and a one-piece molded plastic edge adapter. The edge adapter provides the contoured region to facilitate sample loading, and because it is made from molded plastic is easier to make. Furthermore, the edge adapter has vertically extending arms which define the sides of the loading region and which, when affixed to the back substrate, prevent leakage of buffer solution from the region surrounding the electrophoresis origin. In a preferred embodiment, a groove in the bottom edge of the edge adapter receives the top edge of the front substrate to further define the position of the edge adapter in relation to the substrate. In an alternative embodiment of the invention, vertical divider fins are formed on the contoured surface of the edge adapter. These divider fins define loading wells for the introduction of sample into the lanes of the electrophoresis gel.

DETAILED DESCRIPTION OF THE INVENTION

Figure 1:
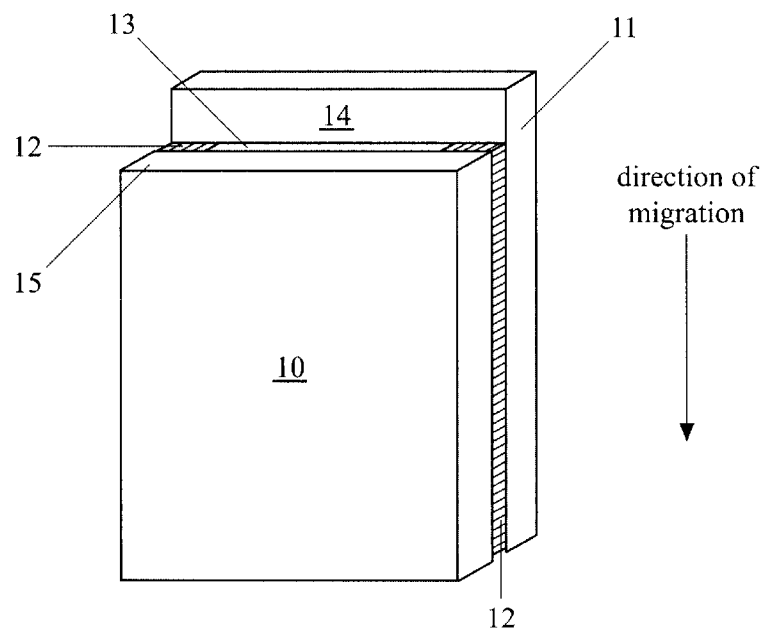
FIG. 1 shows a part of an electrophoresis cassette in accordance with the invention.

The present invention provides electrophoresis cassettes which are formed in two parts. As shown in FIG. 1, the first part of the cassette is an assembled cassette formed from a front substrate 10, a back substrate 11, and spacers 12. The spacers 12 are disposed between the front substrate 10 and the back substrate 11. The front substrate 10 and the back substrate 11 and the spacers are held together in an assembled cassette to define a gel cavity 13. As shown, the length of the front substrate 10 is less than the length back substrate 11 along a direction of migration, thereby leaving a top portion 14 of the back substrate 11 exposed in the assembled cassette. The upper edge 15 of the front substrate 10 preferably is blunt, and is thus more easily manufactured and less susceptible to damage than contoured edges.

Figure 2:
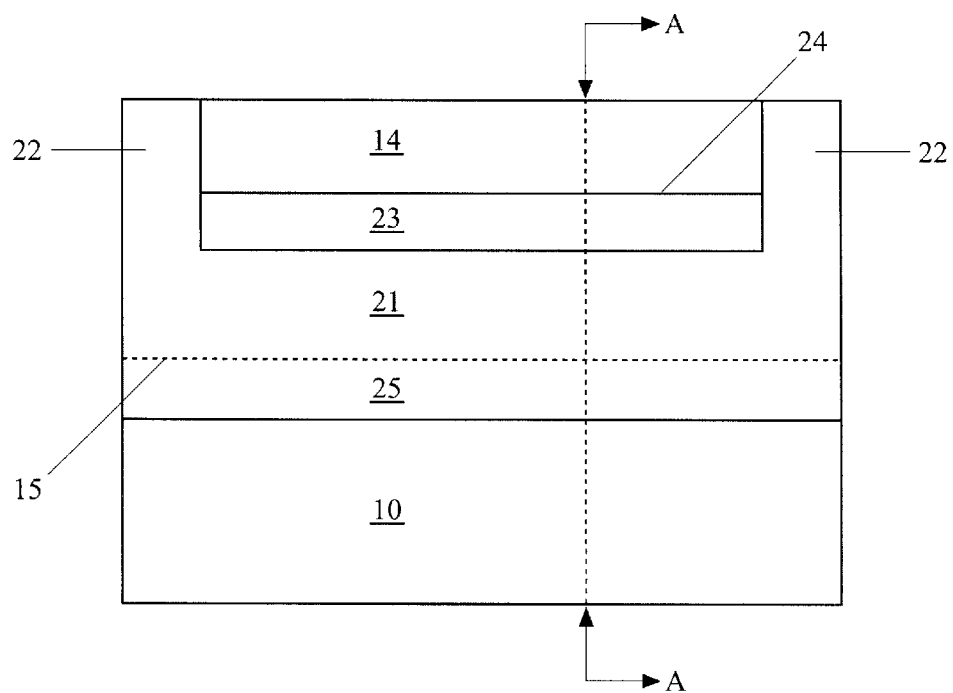
FIG. 2 shows a plan view of an electrophoresis cassette in accordance with the invention.

The second part of the electrophoresis cassette of the invention is an edge adapter which is placed over the upper edge 15 of the substrate 10 to define a loading trough. FIG. 2 shows an exterior plan view of the assembled cassette with an embodiment of the edge adapter in place. The edge adapter has a generally U-shaped profile. While the edge adapter is a single piece, it is convenient to describe the adapter in terms of portions or regions. It will be understood that the separate description of these portions or regions does not mean that they are separable without destruction of the edge adapter.

The, edge adapter has a U shaped main body portion, which is itself made up of a rectangular transverse portion 21 extending from one side edge to the other side edge of the cassette, and two arms 22 extending vertically from opposing ends of the transverse portion 21 towards the top of the edge adapter. The width of the U-shaped main body member is substantially equal to the width of the front and back substrates. The U-shaped main body member has an overall height from the top edge to the bottom edge that is substantially equal to difference between the length of the front and back substrates. Thus, the U-shaped main body member extends upwards from a line parallel to the top edge 15 (shown as a dashed line in FIG. 2) of the front substrate 10 to the tops of the arms which are flush with the top edge of the back substrate.

The edge adapter also includes a contoured region 23 extending along the upper edge of the transverse portion 21 of the U-shaped body member between the arms 22. The contoured.region 23 has a fixed edge which is contiguous with the upper edge of the transverse portion 21 of the U-shaped body member and a free edge 24 disposed opposite to the fixed edge. The edge adapter shown in FIG. 2 also comprises an interlocking portion 25 extending along and being contiguous with the lower edge of the transverse portion 21 of the U-shaped main body member.

Figure 3:
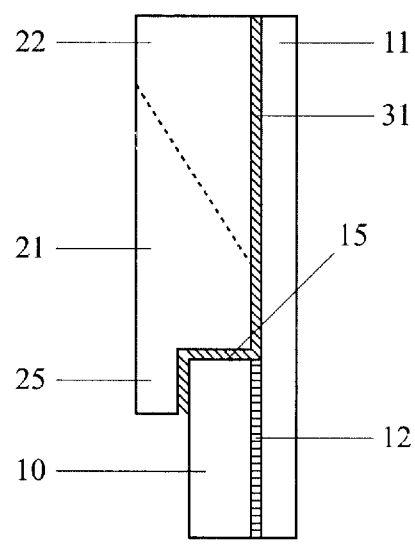
FIG. 3 shows an exterior side view of an electrophoresis cassette in accordance with the invention.

FIG. 3 shows a side end view of the assembled cassette with the edge adapter of FIG. 2 in place. As shown, the interlocking portion 25 and the transverse portion 11 of the U-shaped main body member in concert form a groove that extends transversely along the interior surface of the edge adapter. This groove is sized to receive the upper edge 15 of the front substrate 10, such that the transverse portion 21 and the arms 22 of the U-shaped main body member form an upward extension of the front substrate. The arms 22 are joined to the back substrate 11 by glue 31 which fills the gap having the same width as the gel cavity. This allows the edge adapter to define a space over the top edge of the gel and to prevent buffer leakage from this space in use.

The contoured portion 23 has a contoured surface on the interior surface as indicated by the dashed line in FIG. 3.

Figure 4:
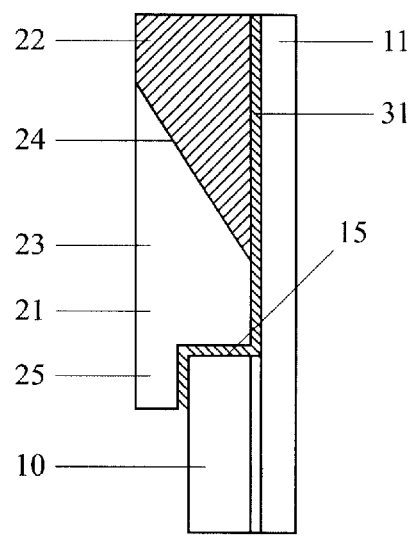
FIG. 4 shows a cross section along line A—A of an electrophoresis cassette in accordance with the invention.
Figure 5:
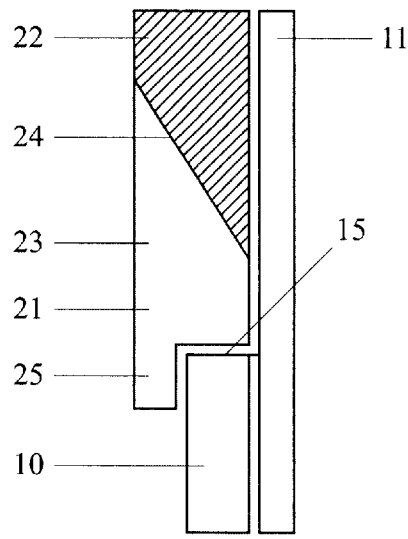
FIG. 5 shows a cross section an alternative embodiment of an electrophoresis cassette in accordance with the invention.

This is more clearly shown in FIG. 4 which shows a cross section view along line A—A in FIG. 2. As can be seen, the contoured region 23 at the fixed edge which is contiguous with the transverse portion 21 has a thickness which is greater than the thickness of the contoured region 23 at the free edge 24, and the contoured region 23 has a height which is less than the height of the arms 22. The shape of the contoured region may be flat, as depicted in FIG. 5, or it may be curved. When flat, the angle formed between the contoured region and the plane of the front substrate (and also the U-shaped main body member) is suitably 30 to 60°, preferably about 45°.

FIGS. 3 and 4 also illustrate the position of the interlocking portion 25, which extends along and is contiguous with the lower edge of the transverse portion 21. The, interlocking portion 25 has a width which is substantially the same as the width of the front and back substrate 10, 11 and a thickness which less than the thickness of the transverse portion 21. The interlocking portion 25 and the lower edge of the transverse portion 21 in concert form a groove extending transversely along the interior surface of the edge adapter. The groove has a thickness which is substantially equal to the thickness of the front substrate 10. Thus, when the edge adapter is disposed with the top edge 15 of the front substrate 10 within the groove and the arms 22 extending upwards over the top portion 14 of the back substrate 11, the contoured edge 23 provides a sample application region for a gel formed within the gel cavity 13.

To use the embodiment of the invention depicted in FIGS. 2–4, a starting cassette structure of the type shown in FIG. 1 is prepared, and the edge adapter is then glued into position to form the finished cassette. Glue 31 is used to fill the gap space between the arms 22 and the back substrate 11, and to affix the top 1 of the front substrate 10 to the abutting portion of the U-shaped main body member, and optionally to the interlocking portion. A suitable adhesive is a UV activated acrylate adhesive such as MINICO® M07950-R (Emerson & Cuming, Inc, Woburn, MA.), which is the same type of adhesive used in the construction of the MICROCEL™ cassettes. As noted below, this glue can contain beads which are used as spacers to define the separation between the substrates. Use of the same glue, with the beads, to affix the arms to the back substrate is desirable as it ensures the same spacing.

The edge adapter also may be releasably affixed to the substrates in a manner which permits it to be removed without destruction of the edge adapter. For example, the edge adapter might be releasably affixed to the substrate using a clamp mechanism, or with a non-hardening adhesive. The use a releasably-affixed edge adapter allows reuse of the edge adapter, if desired. Thus, the term "affixed" encompassed joining the edge adapter to the substrate in both a releasable and a non-releasable (with destruction of the edge adapter) manner.

Gel is then introduced into the gel cassette and polymerized. The cassette is filled to a point where the top of the gel is approximately even with the top edge of the transverse portion 21. As a result, a portion of the edge adapter corresponding to the height of the transverse portion is in contact with the gel. This does not suffer from the difficulties normally associated with the use of plastic because (1) the plastic is remote from the detection sites and thus is unlikely to create spurious fluorescence; (2) the extent of contact with the plastic is small (for example, the height of the transverse portion will generally be less than 10 mm, and preferably less than 5 mm), such that the interference with gel polymerization is minimal; and (3) if necessary, the surface of the edge adapter that will come in contact with the gel can be treated with a surface coating, for example of bindsilane, which will further reduce any interference with polymerization. If desired, a comb may be used to define sample loading wells when the gel is being formed.

FIG. 5 shows an alternative embodiment of the gel cassette of the invention in the same view as FIG. 4. In this case, the height of the transverse portion is substantially reduced (for example to less than 0.5 mm, preferably less than 0.1 mm), such that the length of the effective extension of the front substrate 10 by the edge adapter is much smaller. This further minimizes the risk of significant interaction of the plastic with the polymerizing gel. Furthermore, because the height of the transverse portion is small, the gel can be filled only to the top of the top substrate, without impairing the ability to load samples. In this case, the edge adapter maybe attached to the starting cassette structure before or after filling with the gel.

Figure 6:
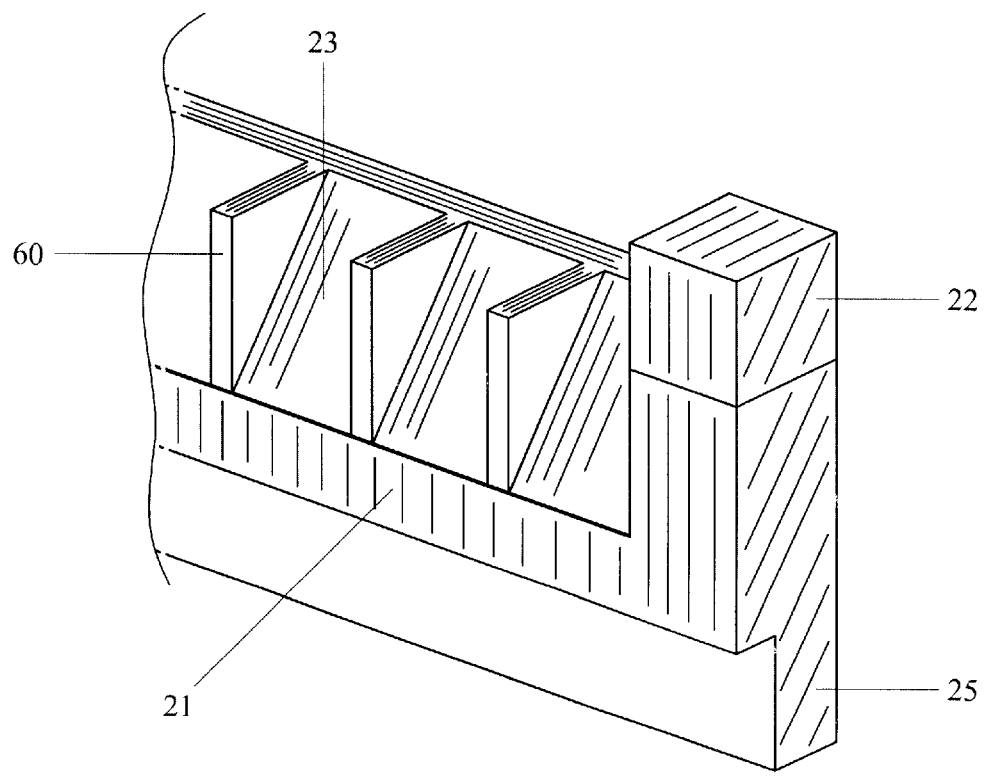
FIG. 6 shows a perspective view of an embodiment of the edge adapter with molded loading wells.

FIG. 6 shows a perspective view of an embodiment of the edge adapter with molded loading wells. Thus, in this case dividers 60 are formed on interior of the contoured region 23, extending from the upper edge of the transverse portion 21 to the top of the contoured region 23. Arms 22 are disposed at each end of the contoured region 23. The wells facilitate the introduction of sample into the lanes of the gel cassette. The transverse portion in this embodiment is preferably short, for example having a height of less than 0.5 mm, and more preferably less than 0.1 mm.

Figure 7:
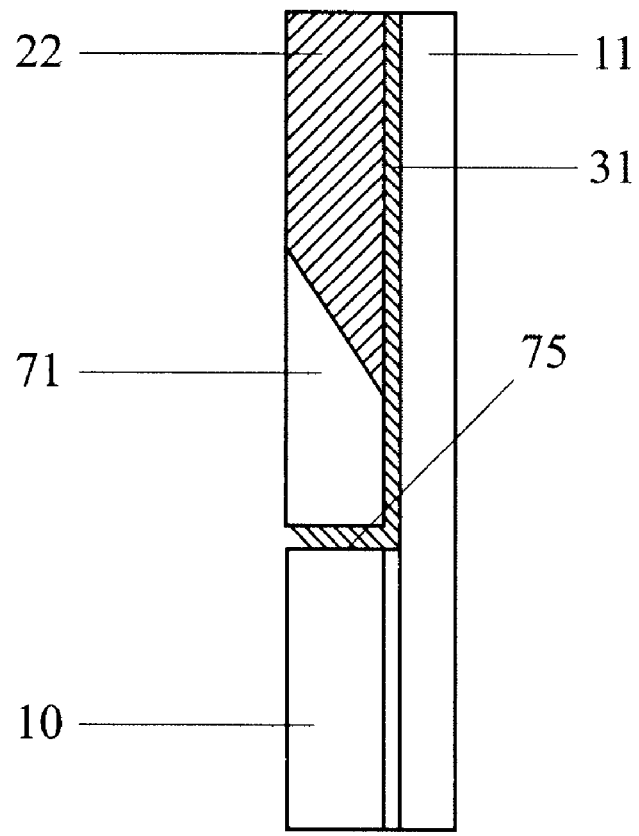
FIG. 7 shows a cross-section of another embodiment of an electrophoresis cassette in accordance with the invention.

FIG. 7 shows a cross-sectional view of another embodiment of the invention. This embodiment differs from the previous embodiments in that it lacks the interlocking portion. Thus, the transverse portion 71 of the edge adapter abuts against the entire top edge 75 of the front substrate 10. Other portions of the electrophoresis cassette are the same.

The edge adapter in each of the foregoing embodiments is a single piece structure which is preferably made from plastic. Suitable plastics are rigid moldable plastics which will have minimal interaction with the chemical reagents used in preparation of polyacrylamide gels. Specific plastics which may be used include acrylics, polycarbonates and the like. Preferably, the edge adapter is formed as a single integral piece by a molding process. However, it is not outside the scope of the invention to fabricate several separate molded plastic pieces for assembly into an edge adapter having a structure as described above. Thus, as used in the specification and claims of this application, the term "single piece of molded plastic" refers to edge adapters which are integrally formed as a single piece, and edge adapters which are assembled from two or more pre-formed pieces into an assembled whole[]which cannot be non-destructively disassembled.

The foregoing discussion describes various embodiments of an edge adapter and gel cassette in accordance with the invention. In doing so, little attention was given to the specific assembly of the starting gel cassette structure of FIG. 1. This structure may be prepared in any of the numerous ways known in the art, including but not limited to glue line spacers as described in commonly, assigned U.S. Pat. No. 5, 627,022 and as used in commercially available MICROCEL™ cassettes, glued fiber spacers as described in commonly assigned U.S. Pat. Nos. 5,618,398 and 5,599,434, and polyester or MYLAR® spacer strips or gaskets, as disclosed in U.S. Pat. No. 5,993,628. When a U-shaped spacer (for example of polyester is used), only one spacer is required. When glue line spacers are used, the glue contains inert beads, for example glass beads, whose size determines the separation between the glass plates. Typically, the size of these beads is 20 µm or 50 µm. The starting gel cassette may be constructed with or without interior lane dividers.

What is claimed is:

1. An electrophoresis cassette comprising:
   (a) a front substrate and a back substrate each having a width in a direction transverse to a direction of migration, and a length parallel to the direction of migration;
   (b) at least one spacer disposed between the front and back substrates to define an assembled cassette having an electrophoresis gel cavity;
   (c) an edge adapter affixed to the front and back substrates, where the length of the front substrate is less than the length of the back substrate, thereby leaving a top portion of the back substrate exposed in the assembled cassette;
     wherein the edge adapter comprises a generally U-shaped main body having a transverse portion and two arms extending vertically from opposing ends of the transverse portion, having an overall height substantially equal to the difference between the length of the front substrate and the back substrate, said edge adapter having a contoured region extending along and proximal to an upper edge of the transverse portion of the U-shaped body member, said contoured region having a thickness at the edge proximal to the transverse portion greater than the thickness at the edge distal to the transverse portion, and where said contoured region provides a sample application region bounded by said contoured region and said back substrate for a gel formed within the gel cavity.

2. The electrophoresis cassette of claim 1, wherein the transverse portion has a thickness which is greater than the thickness of the front substrate, and
   the edge adapter further comprises an interlocking portion extending along and being contiguous with the lower edge of the transverse portion of the U-shaped main body member, said interlocking portion having a width which is substantially the same as the width of the front and back substrate and a thickness which less than the thickness of the transverse portion, and wherein the interlocking portion and the lower edge of the transverse portion in concert form a groove extending transversely along the interior surface of the edge adapter, said groove having a thickness which is substantially equal to the thickness of the front substrate, and wherein the upper edge of the front substrate is disposed within the groove.

3. The electrophoresis cassette of claim 2, wherein the front and back substrates are glass.

4. The electrophoresis cassette of claim 2, wherein the transverse portion of the U-shaped main body member has a height of less than 10 mm.

5. The electrophoresis cassette of claim 4, wherein the transverse portion of the U-shaped main body member has a height of less than 5 mm.

6. The electrophoresis cassette of claim 2, wherein the edge adapter is an integrally-formed molded plastic piece.

7. The electrophoresis cassette of claim 2, wherein the edge adapter is affixed to the front and back substrates with glue.

8. The electrophoresis cassette of claim 7, wherein the arms are affixed to the back substrate with glue containing spacer beads.

9. The electrophoresis cassette of claim 2, wherein the surface of the contoured region proximal to the back substrate is flat.

10. The electrophoresis cassette of claim 9, wherein the contoured region intersects of a plane defined by the front substrate at an angle of from 30° to 60°.

11. The electrophoresis cassette of claim 2, further comprising a plurality of dividers, extending from the surface of the contoured region proximal to the back substrate, thereby creating loading wells.

12. The electrophoresis cassette of claim 11, wherein the transverse portion of the U-shaped main body member has a height of less than 0.5 mm.

13. The electrophoresis cassette of claim 12, wherein the transverse portion of the U-shaped main body member has a height of less than 0.1 mm.

14. The electrophoresis cassette of claim 11, wherein the edge adapter is an integrally-formed molded plastic piece.

15. The electrophoresis cassette of claim 1, further comprising a plurality of dividers, extending from the surface of the contoured region proximal to the back substrate, thereby creating loading wells.

16. An edge adapter for creating a sample loading region on an electrophoresis gel, wherein the edge adapter is a single piece of molded plastic having an interior surface, an exterior surface, and top, bottom and side edges, said edge adapter comprising:
   a U-shaped main body portion having a rectangular transverse portion extending from one side edge to the other side edge and two arms extending vertically from opposing ends of the transverse portion towards the top of the edge adapter, said transverse portion having an upper edge extending transversely between the two arms, a lower edge, and a thickness; and
   a contoured region extending along the upper edge of the transverse portion of the U-shaped body member between the arms, said contoured region having a thickness at the edge proximal to the transverse portion greater than the thickness at the edge distal to the transverse portion.

17. The edge adapter of claim 16, further comprising an interlocking portion extending along and being contiguous with the lower edge of the transverse portion of the U-shaped main body member, said interlocking portion having a thickness which less than the thickness of the transverse portion, and wherein the interlocking portion and the lower edge of the transverse portion in concert form a groove extending transversely along the interior surface of the edge adapter.

18. The edge adapter of claim 17, wherein the transverse portion of the U-shaped main body member has a height of less than 10 mm.

19. The edge adapter of claim 18, wherein the transverse portion of the U-shaped main body member has a height of less than 5 mm.

20. The edge adapter of claim 17, wherein the edge adapter is an integrally-formed molded plastic piece.

21. The edge adapter of claim 17, wherein the interior surface of the contoured region is flat.

22. The edge adapter of claim 21, wherein the contoured region intersects of a plane defined by the U-shaped main body member at an angle of from 30° to 60°.

23. The edge adapter of claim 17, further comprising a plurality of dividers, extending from the interior surface of the contoured region, thereby creating loading wells.

24. The edge adapter of claim 16, further comprising a plurality of dividers, extending from the interior surface of the contoured region, thereby creating loading wells.

25. An electrophoresis cassette comprising:
   (a) a front and rear substrate;

(b) at least one spacer disposed between the front and rear substrate, said substrates and said at least one spacer being held together in an assembled cassette to define an electrophoresis zone with a thickness corresponding to the thickness of the spacer; and (c) an edge adapter affixed to the front and rear substrates to define a sample well, wherein the edge adapter defines the thickness of the sample well as being of a thickness greater than that of the spacer, where the length of the front substrate is less than the length of the rear substrate, thereby leaving a portion of the rear substrate exposed in the assembled cassette.

26. An electrophoresis cassette according to claim 25, wherein the front and rear substrate each have a planar interior surface which face one another in the assembled cassette.

\* \* \* \* \*